US008790371B2

(12) United States Patent
Dyer et al.

(10) Patent No.: US 8,790,371 B2
(45) Date of Patent: Jul. 29, 2014

(54) DYNAMIC LOGARITHMIC SPINAL DECOMPRESSION TABLE AND METHOD

(76) Inventors: Allan E. Dyer, Oldsmar, FL (US); Lawrence A. Dyer, Oldsmar, FL (US)

( * ) Notice: Subject to any disclaimer, the term of this patent is extended or adjusted under 35 U.S.C. 154(b) by 149 days.

(21) Appl. No.: 13/121,908

(22) PCT Filed: Sep. 30, 2008

(86) PCT No.: PCT/US2008/011284
§ 371 (c)(1),
(2), (4) Date: Jun. 27, 2011

(87) PCT Pub. No.: WO2010/039105
PCT Pub. Date: Apr. 8, 2010

(65) Prior Publication Data
US 2011/0270310 A1    Nov. 3, 2011

(51) Int. Cl.
*A61H 1/00* (2006.01)
*A61F 5/00* (2006.01)

(52) U.S. Cl.
USPC ............................. 606/241; 606/242; 602/32

(58) Field of Classification Search
CPC .... A61F 5/055; A61H 1/0218; A61H 1/0222; A61H 2203/0468; A61H 2201/1607; A61H 2203/0456; A61H 1/02; A61H 2001/1611; A61H 2001/1623; A61H 2001/1626; A61H 2001/5007; A61H 2205/04; A61H 2205/081; A61G 13/009

USPC ........ 601/23, 24, 26; 606/53, 54, 57, 58, 237, 606/240, 241, 242, 243, 245; 602/32, 33, 602/35, 36, 38

See application file for complete search history.

(56) References Cited

U.S. PATENT DOCUMENTS

| 3,194,232 | A | 7/1965 | Rickenbach |
| 5,569,176 | A | 10/1996 | Graham |
| 6,039,737 | A | 3/2000 | Dyer |
| 6,152,950 | A * | 11/2000 | Shealy et al. ................. 606/243 |
| 6,740,055 | B2 | 5/2004 | Dominguez |
| 6,939,269 | B2 | 9/2005 | Makofsky |
| 7,189,214 | B1 | 3/2007 | Saunders |

* cited by examiner

*Primary Examiner* — Quang D Thanh (57) ABSTRACT

A logarithmically increasing decompression force is applied to a spinal column in a progressively changing direction lying in the mid-sagittal plane. This focuses the decompression force as compared with a straight-line pull. A table to achieve this decompression force has a fixed table section, a moveable table section, a reciprocating arm which acts as a movable pre-tension section, a vertically adjustable upstanding support supported by the pre-tension section, an attachment point attached to a tensionometer-head associated with the upstanding support for attachment to a harness, a moveable table section drive for extending the moveable table section from the fixed table section and for retracting the moveable table section toward the fixed table section, a reciprocating arm drive for extending and retracting the reciprocating arm from the movable table section, and an upstanding support drive for driving the upstanding support to different vertical positions.

17 Claims, 15 Drawing Sheets

DYNAMIC LOGARITHMIC SPINAL DECOMPRESSION TABLE AND METHOD

BACKGROUND

Back pain is among the most common conditions for which patients seek medical care. More than 70 percent of adults suffer back pain or neck pain at some time in their lives. In the United States, medical treatment of back pain is estimated to cost $25 billion dollars annually. Workers compensation costs and time lost from work add another $25 billion.

Medical management is the first treatment choice. If there is no improvement in the patient's condition, surgery is often the next treatment of choice. Despite the uncertainty about how effective surgery is for patients, the number of fusion surgeries rose 127% from 1997 to 2004, to more than 303,000. Recent research demonstrates that even after two years patients treated conservatively are as well off as those treated surgically. Surgical costs are continuing to rise, as patients receive ever more aggressive treatments.

Recently, vertebral axial decompression therapy for the spine and discs has emerged as a frontline treatment for back pain. This is a non-surgical treatment for herniated discs, degenerative disc disease, posterior facet syndrome and failed back surgery. With traditional traction therapy, forces are applied in a linear fashion and the resultant muscle guarding prevents the discs from being decompressed. Paraspinal muscles are conditioned to oppose abrupt and linear changes in tension, but will relax if the force is applied in a smooth gradual manner whereby the rate is slowed progressively according to a logarithmic time scale.

It has been shown that tension forces to the spine applied in a 'logarithmic' time/force curve will decompress the discs and spine. Vertebral axial decompression is the only treatment that has been shown in clinical study to decrease the intervertebral disc pressure to negative levels and to decompress the lateral nerve roots that supply the legs.

While this known vertebral axial decompression therapy is advantageous, an improved vertebral decompression therapy would be desirable.

SUMMARY

A logarithmically increasing decompression force is applied to a spinal column in a progressively changing direction lying in the mid-sagittal plane. This allows the decompression force to be focused on selective vertebrae.

A table to achieve this decompression force has a fixed table section, a moveable table section, a vertically adjustable upstanding support supported by the moveable table section, an attachment point associated with the upstanding support for attachment to a harness; a first drive for extending the moveable table section from the fixed table section and for retracting the moveable table section toward the fixed table section, and a second drive for driving the upstanding support to different vertical positions.

Other features and advantages will be apparent from the following description in conjunction with the drawings.

BRIEF DESCRIPTION OF THE DRAWINGS

In the figures which illustrate example embodiments of the invention.

DETAILED DESCRIPTION

Figure 1:
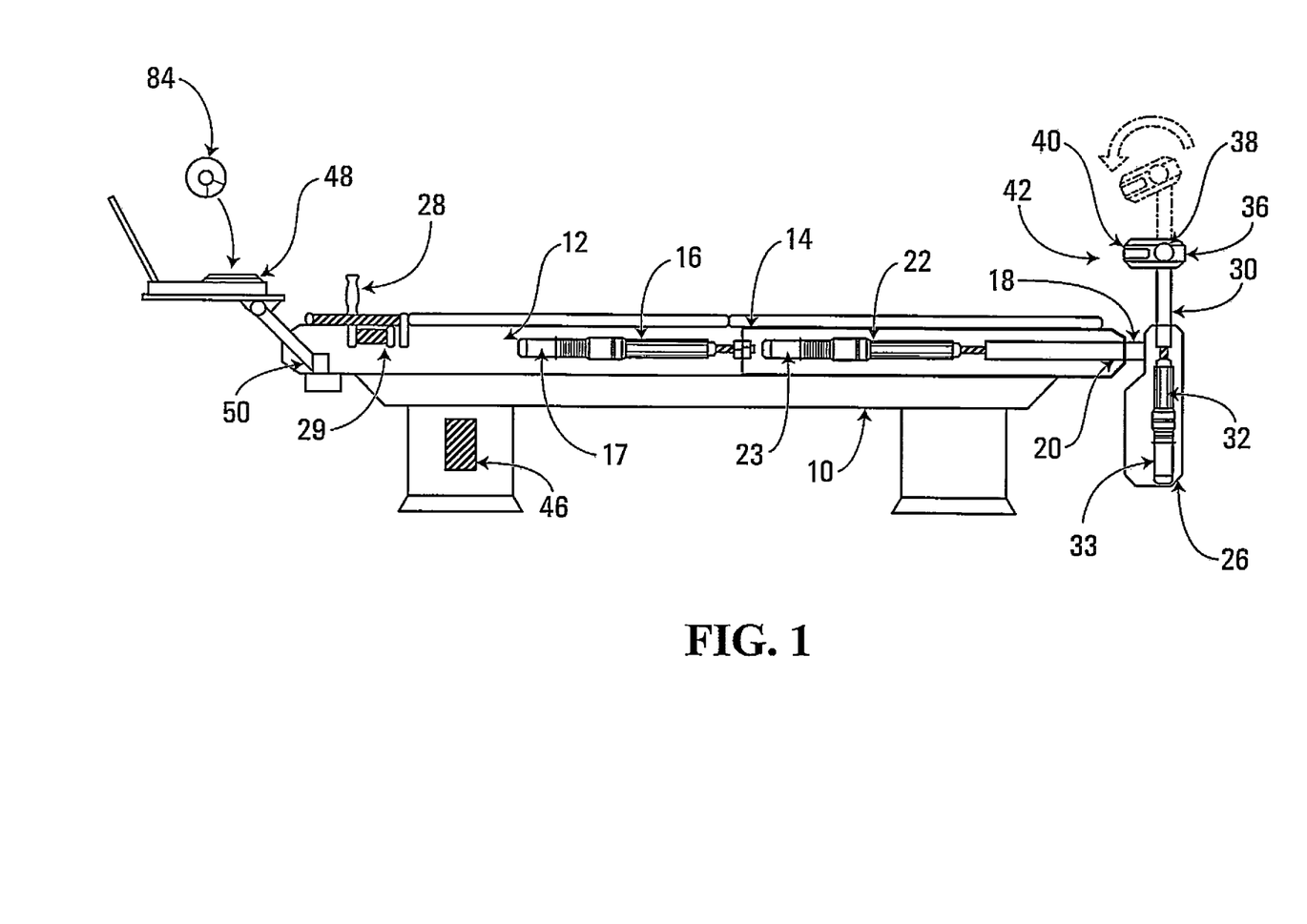
FIG. 1 is a schematic side view of a vertebral decompression table made in accordance with this invention.

Turning to FIG. 1, a vertebral decompression table 10 has a fixed table section 12 and a moveable table section 14. The fixed table section 12 has a linear actuator 16 which may be activated to push the moveable table section 14 away from the fixed table section 12 or draw the moveable table section 14 toward the fixed table section 12. The fixed table section also has a pair of handgrips 28. A motor 29 controls the longitudinal position of these handgrips. The moveable table section has a reciprocating arm 18 which may be extended outwardly from the end 20 of the moveable table section 14 or retracted inwardly toward the end 20 of the moveable table section by a linear actuator 22 housed within the moveable table section. The base 26 of a vertically adjustable support 30 is joined to arm 18. Base 26 houses a linear actuator 32 which may extend support 30 upwardly or retract support 30 downwardly.

A tensionometer-head 36 is pivotably attached to the vertically adjustable support 30 at horizontal pivot 38 so that the tensionometer-head may pivot up and down. The tensionometer-head 36 houses a tensionometer 40 with a protruding attachment 42 for attachment to a harness. The attachment may be a protruding metal tang with a central opening to connect to a seat-belt like buckle.

Each of linear actuators 16, 22, and 32 are operatively connected to a controller 46. The controller 46 is input by the output of the tensionometer 40 and the output of positional encoders 17, 23, and 33 attached to each linear actuator 16, 22, and 32, respectively. The controller is operatively connected to a personal computer 48 which is pivotably mounted to the fixed table section 12 on arm 50.

Controller 46, which may be a microprocessor, and computer 48 may be loaded with software from a computer readable media such as CD 84.

Figure 2:
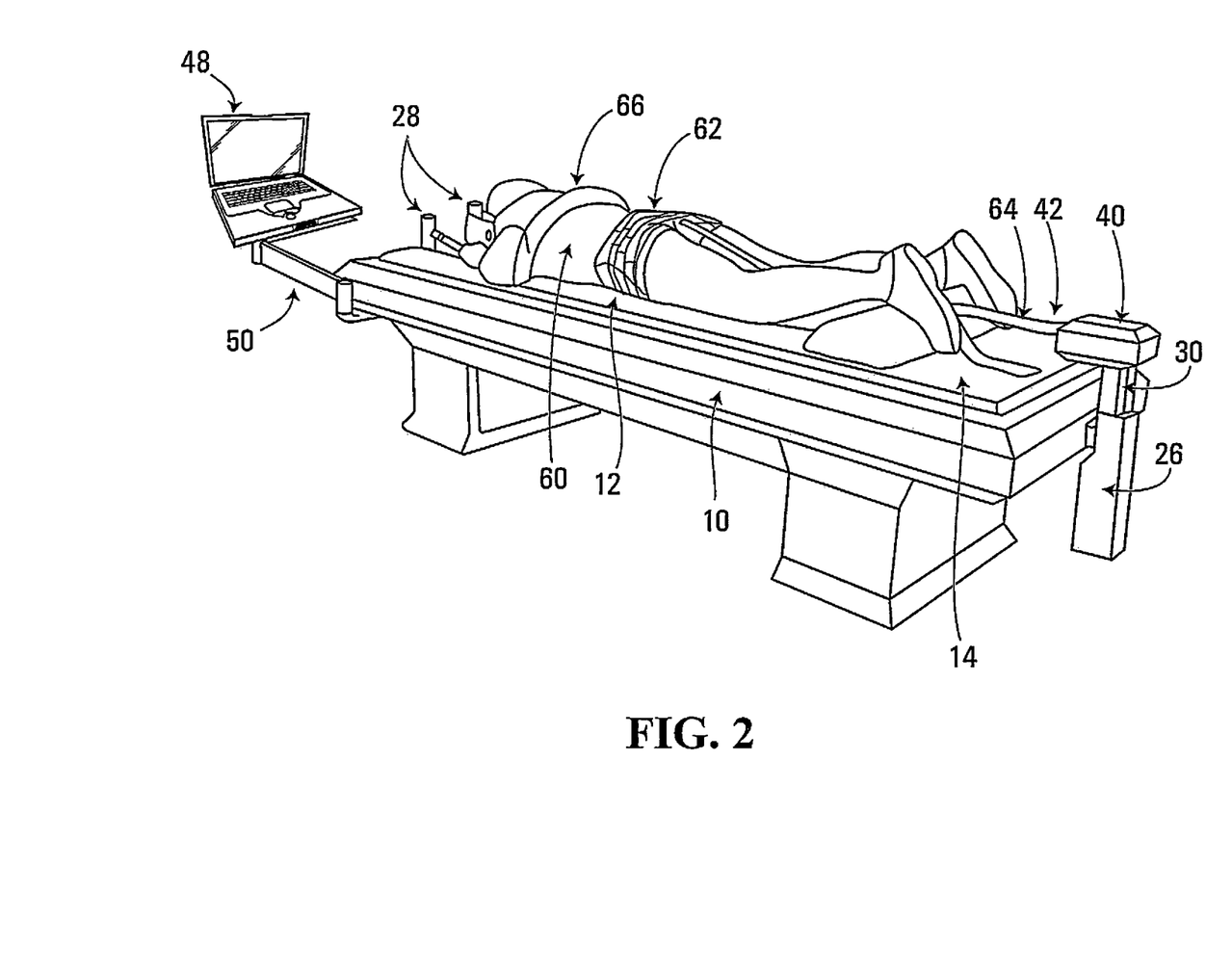
FIGS. 2 and 3 are perspective views of the table of FIG. 1 shown in use.
Figure 3:
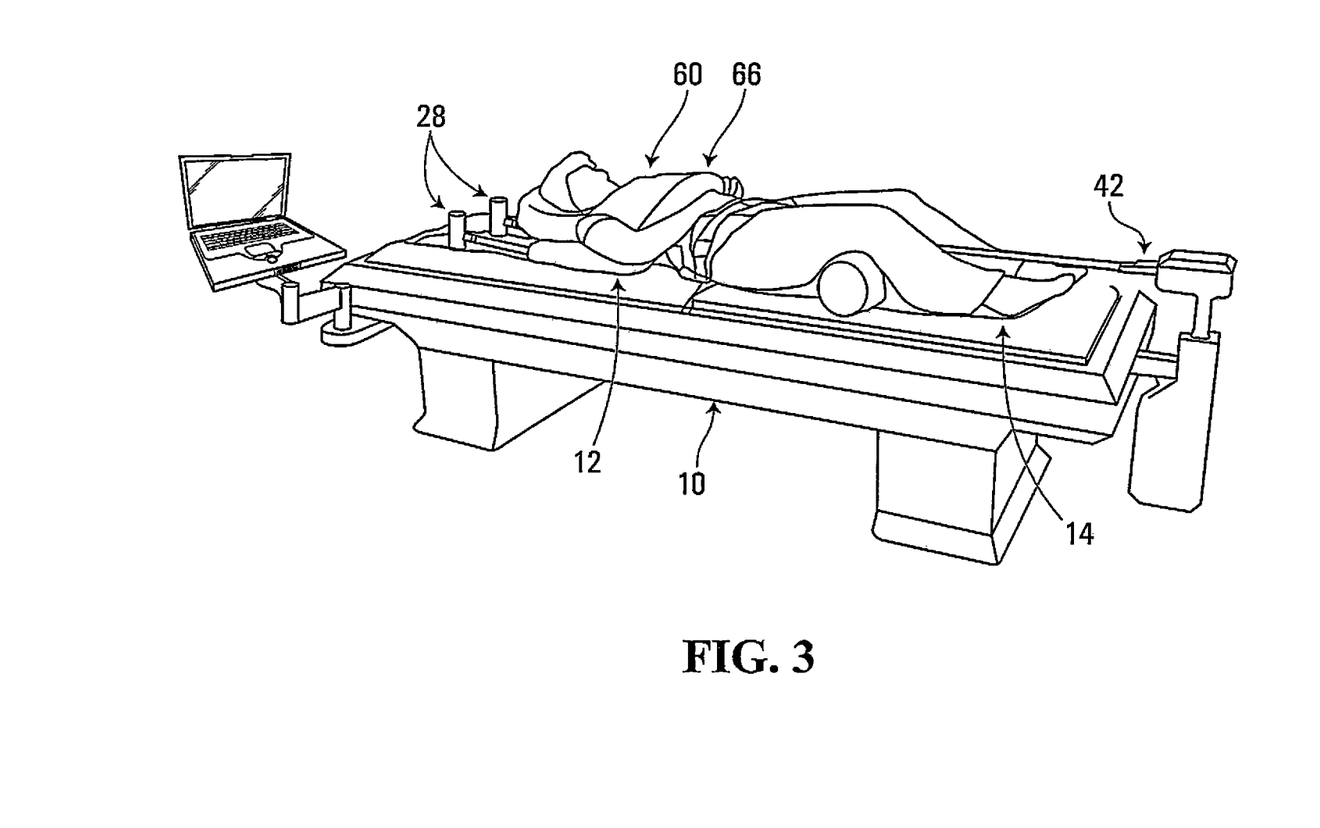

Turning to FIG. 2, a patient 60 may lie prone on table 10, with feet facing tensionometer 40. The patient wears a pelvic harness 62 with straps 64 attached to attachment 42 of the tensionometer. A suitable pelvic harness is described in U.S. Pat. No. 5,115,802 issued May 26, 1992, the contents of which are incorporated herein by reference. The patient's upper body may be restrained by wearing a thoracic restraint 66 attached to handgrips such that the handgrips act as mounts. Alternatively, or additionally, the patient may grip the handgrips 28. Similarly, as shown in FIG. 3, a patient 60 may lie in a supine position on table 12 with feet facing the tensionometer. As in the prone position, the patient may wear a pelvic harness attached to attachment 42 and a thoracic restraint 66 attached to handgrips 28.

Figure 4:
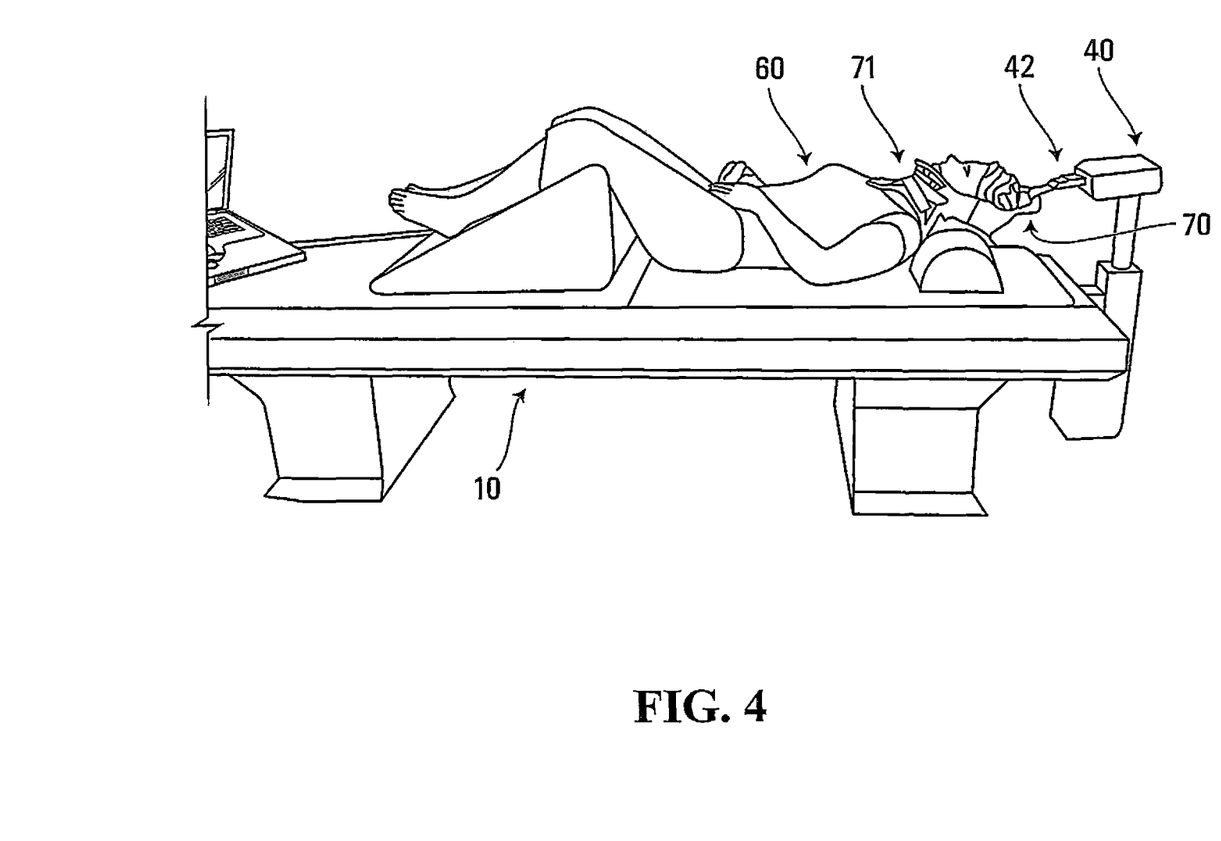
FIG. 4 is a perspective partial view of the table of FIG. 1 shown in use.

With reference to FIG. 4, as a further alternative, the patient 60 may lie in a supine position on table 10 with their head facing tensionometer 40. In this instance, the patient may wear a cervical-head harness 70 composed of a support collar 71 and anchor strap assembly attached to attachment 42 of the tensionometer 40. In this orientation, there is no need to tether the body of the patient to the table because the decompression forces applied by the table to the head and neck are too low to overcome body weight.

Figure 5:
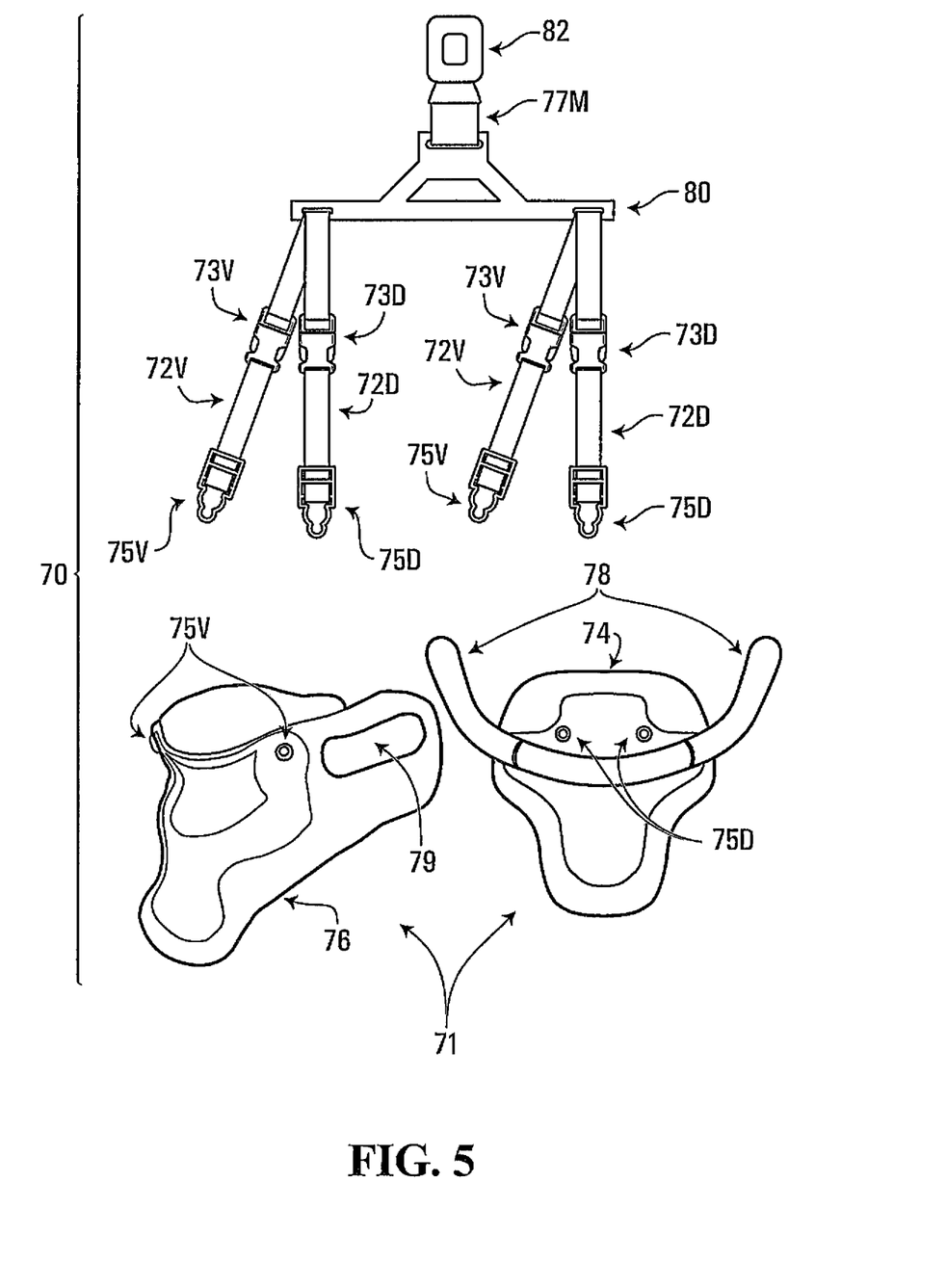
FIG. 5 is an exploded view of the cervical-head harness.
Figure 6:
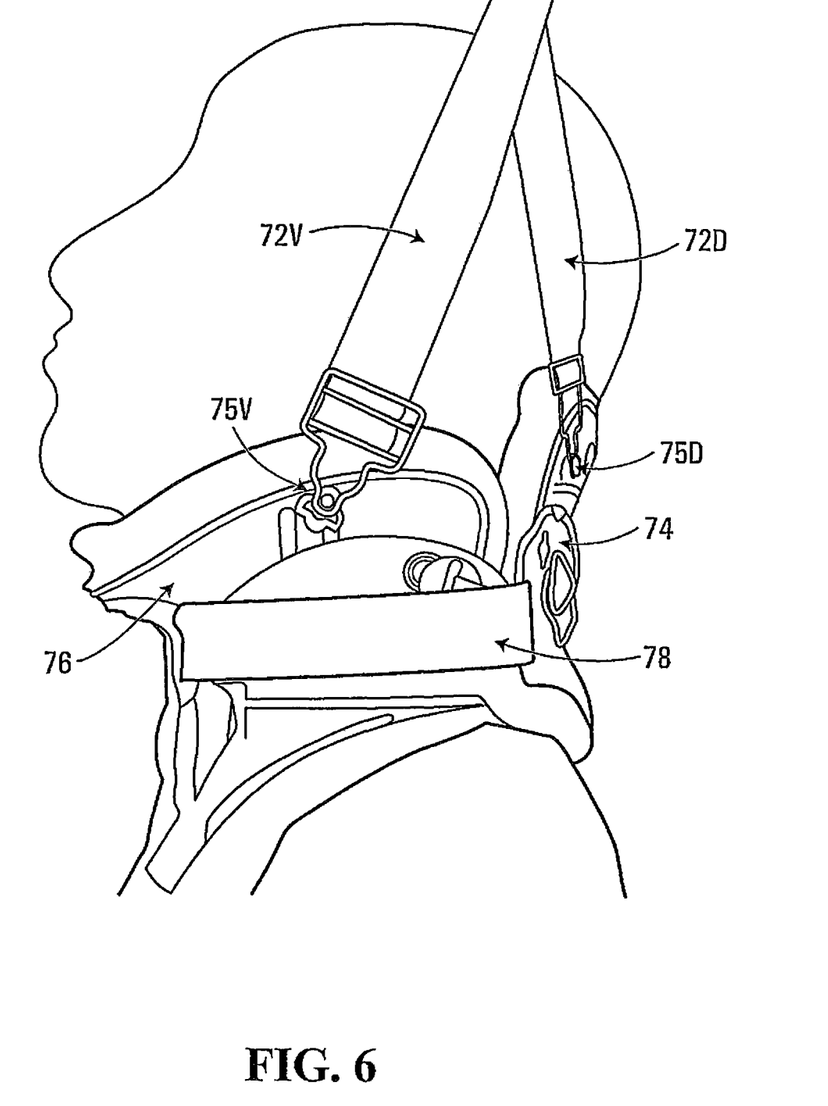
FIG. 6 is a side view of the cervical-head harness shown in FIG. 5.
Figure 7:
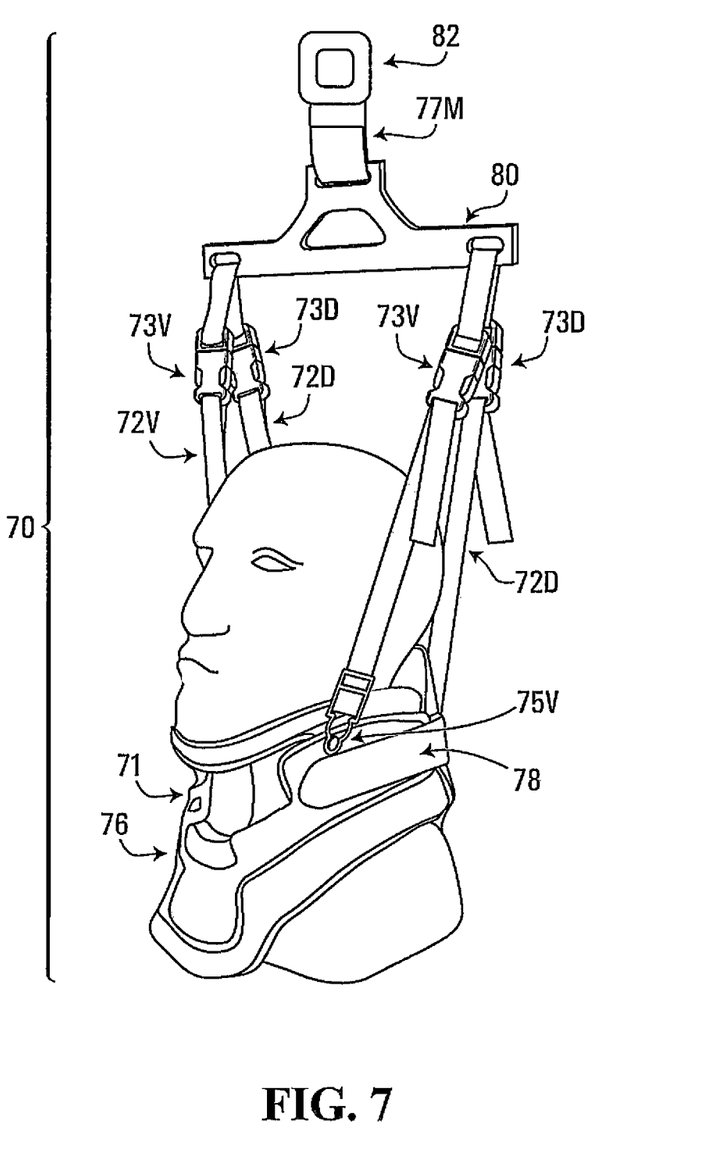
FIG. 7 is an angled view of an integrated cervical-head harness and anchor strap assembly which may be used with the table of FIG. 1.

The cervical-head harness 70 is detailed in FIGS. 5, 6, and 7. Turning to these figures, collar 71 has a curved dorsal member 74 and a curved ventral member 76. A strap 78 extends from each side of the dorsal member and is provisioned with hook fasteners. A loop fastener strap 79 is attached to each side of the ventral member. Thus, the dorsal and ventral members may be placed around the neck of a patient and the straps 78, 79 connected with a hook-and-loop (VELCRO™) attachment. Many alternate arrangements for the cervical collar are possible. For example, a single piece flexible collar could be flexed to allow placement around the neck of a patient and then the free ends joined by straps to complete its attachment to a patient.

As part of the anchor strap assembly, a pair of straps 72D extend from the dorsal member to a crossbar 80 and a second pair of straps 72V extend from the ventral member to the crossbar. When the cervical collar is properly positioned, these straps extend on either side of the head of the patient with the dorsal member straps 72D directly behind the ventral member straps 72V. Also, with the collar properly positioned on the patient, the attachment connectors 75V of the ventral straps 72V lie below the patient's mandible and between the chin and the ear of the patient. The attachment connectors 75D of the dorsal straps 72D lie below the patient's occiput on each side. The straps 72D, 72V extend upwardly and slightly outward from their attachment points to the crossbar 80. A main strap 77M extends from the middle of the crossbar and terminates in a buckle 82. The straps 72D and 72V are adjustable in length, and can be tightened or loosened independently by adjustable connectors 73V and 73D. The dorsal straps may be tightened more than the ventral straps in order to apply more force to the occiput of the head. Alternatively, the ventral straps may be tightened more than the dorsal straps in order to direct and apply more force to the patient's mandible. Straps may also be tightened or loosened from left side or right side, to direct the force more to one side.

Returning to FIG. 1, with the patient tethered to the table 10, the operator may enter via computer 48 a pre-tension, a maximum tension, a starting and ending height, a cycle time, the time to reach maximum tension (i.e., the time for the decompression phase), and the time to return to the pre-tension (i.e., the time for the retraction phase). Then, once the operator presses a start button, the controller will first control linear actuator 32 to adjust the height of the tensionometer-head 36 to match the entered starting height. Next, the controller 46 will operate linear actuator 22 to extend arm 18 in order to linearly increase the distracting tension on the patient's spine, up to the pre-tension. A tension feedback signal from the tensionometer 40 allows the controller to apply an appropriate drive signal to the linear actuator 22 to achieve this result. With lumbar treatments, when the pre-tension has been achieved, the controller may then activate both linear actuator 16 in order to increase the separation of the table halves and linear actuator 32 in order to move the tensionometer-head 36 vertically. These movements are controlled so that the tensionometer-head moves in an arc toward the specified ending height and so that the tension on the patient's spine logarithmically increases to the specified maximum tension. After reaching the maximum tension, the controller controls linear actuators 16 and 32 to move the tensionometer-head in the same arc back to its initial position in a retraction phase in order to reduce the tension logarithmically to the pre-tension. Indeed, as the head 36 returns to its initial position; the tension may begin to fall below the desired pre-tension and so, the controller controls linear actuator 22 in order to maintain the desired pre-tension at the end of the retraction phase. The controller may then repeat the cycle to maximum force and back to pre-tension. Once a specified number of cycles have been completed, the controller, after a rest phase at the pre-tension, releases the pre-tension.

Figure 8:
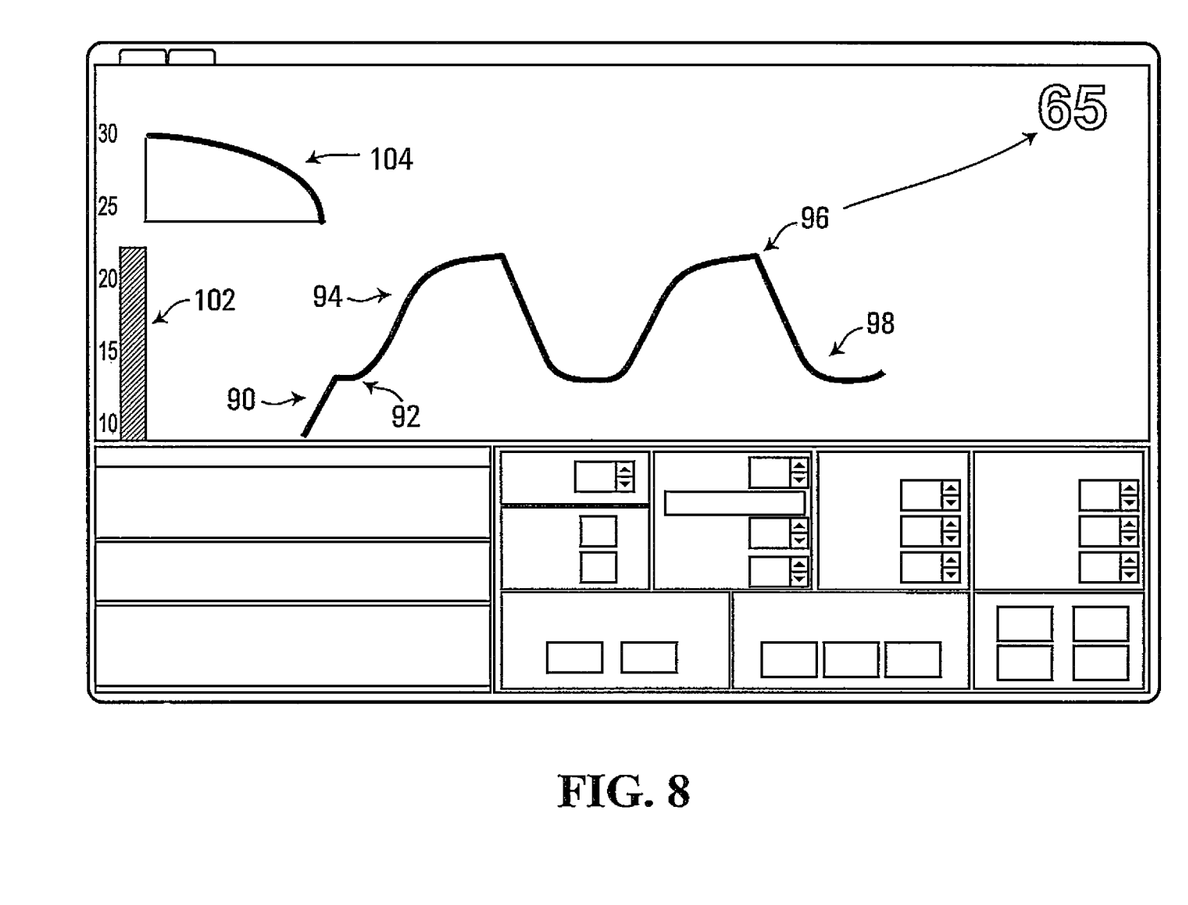
FIG. 8 is a screen shot from a computer display associated with the table of FIG. 1, FIGS. 9 and 10 are schematic side partial view of the table of FIG. 1 illustrating its operation.

As the table operates, the computer 48 may display a tension versus time curve as shown in FIG. 8. Turning to FIG. 8, curve segment 90 shows the linear increase in the tension to the pre-tension amount. Following a short rest segment 92 at the pre-tension level, segment 94 shows the tension increasing logarithmically to the maximum tension at point 96. Segment 98 shows the tension thereafter logarithmically decreasing back to the pre-tension amount. After a rest period, a new cycle commences. The computer may also display the current height of the tensionometer-head 36 above the plane of the table with bar 102.

The tensionometer provides a mechanism for registering the reaction of the spinal column structures as the distraction tension is applied progressively along the spinal column. Reactions such as release of facets, myofascial strictures, and/or compressive lesions register immediately as irregularities or deviations in an otherwise smooth display captured in the displayed time versus tension curve. The controller quickly adjusts so that the reactions register as brief irregularities.

Figure 9:
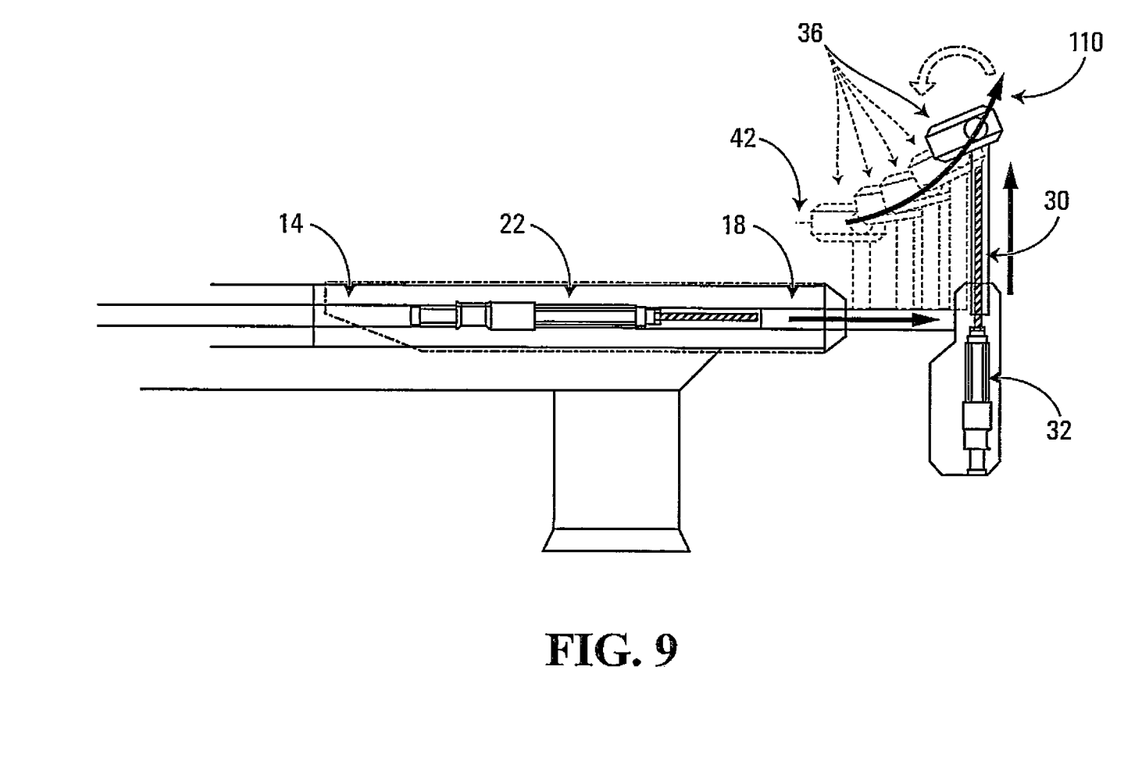
Figure 10:
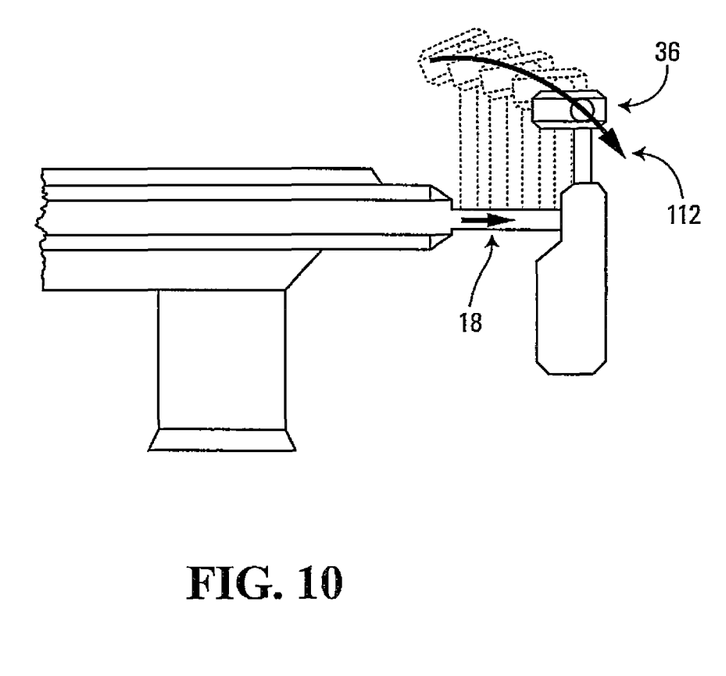

If the starting height is lower than the ending height, the arc followed by the tensionometer-head 36 will be an ascending arc, as shown in FIG. 9 at 110. If the starting height is higher than the ending height, the arc followed by the tensionometer-head 36 will be a descending arc, as shown in FIG. 10 at 112. Notably, as seen in FIG. 9, the tensionometer-head 36 pivots so that the attachment point 42 always aligns with the patient. This ensures that the tensionometer will accurately measure the applied tension. The display of FIG. 8 may also indicate whether the arc is ascending or descending. In particular, FIG. 8 illustrates at 104 a descending arc.

Figure 11:
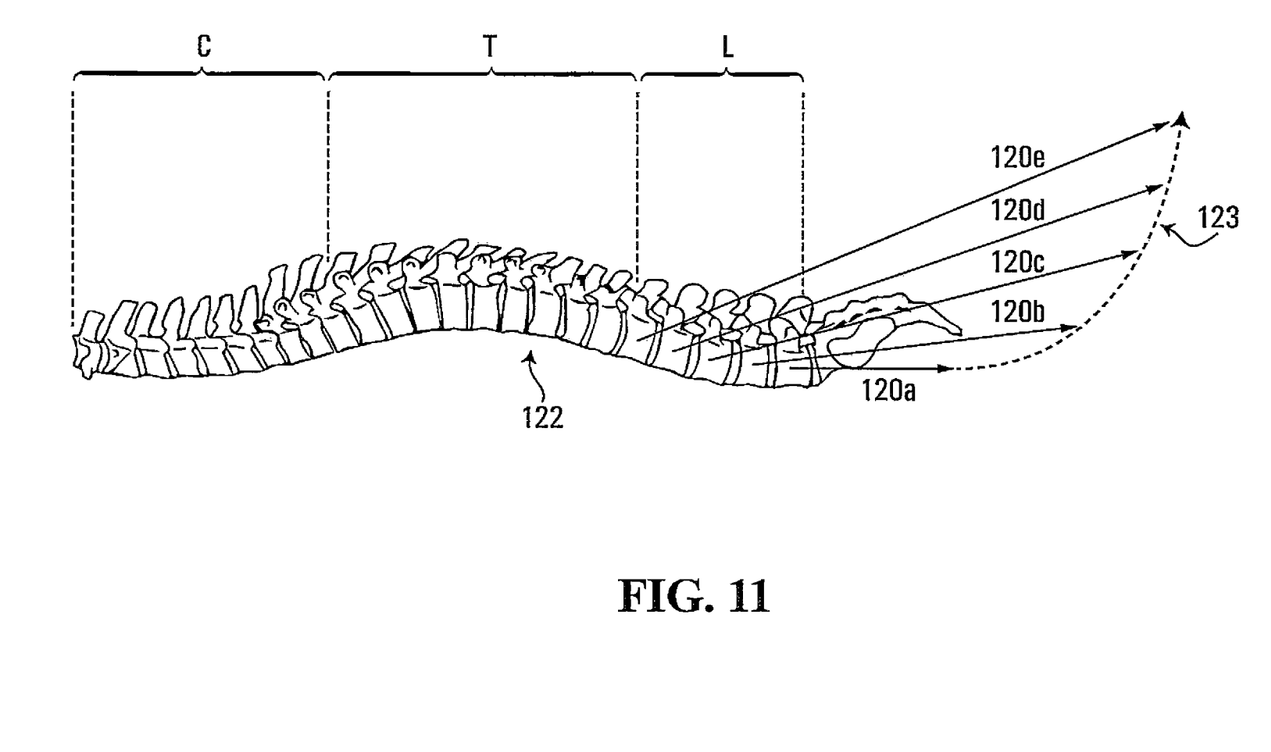
FIGS. 11, 12, 13 and 14 are force vector diagrams illustrating operation of the table of FIG. 1.
Figure 12:
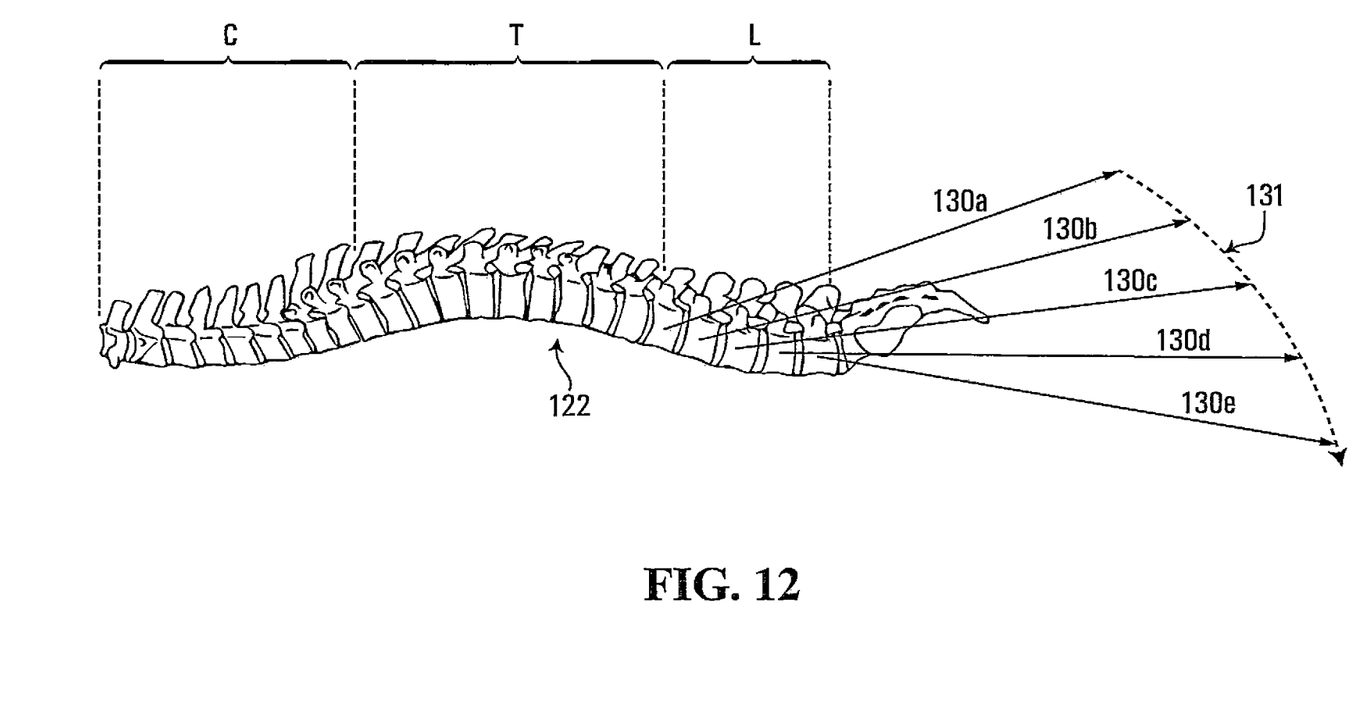

As shown in FIG. 11, the patient's spine has cervical vertebrae C, thoracic vertebrae T, and a lumbar vertebrae L. With a patient lying prone on table 10 and tethered to the tensionometer-head 36 of the table, with a pelvic harness 62 as shown in FIG. 2, FIG. 11 shows the ascending force vectors 120a, 120b, 120c, 120d, 120e progressively applied to the patient's spine 122 during logarithmic tension increase where the tensionometer-head 36 follows an ascending arc 123. FIG. 12 shows the descending force vectors 130a, 130b, 130c, 130d, 130e progressively applied to the patient's spine during logarithmic tension increase where the tensionometer-head 36 follows a descending arc 131. It will be apparent that these force vectors lie in the mid-sagittal plane of the patient and, with the table top horizontal, this mid-sagittal plane will be a vertical plane.

The progressively ascending and increasing force illustrated in FIG. 11 (applied to the spine of a person in the prone position) tends to increase the lordotic curvature of the lumbar spine L on an anterior/posterior plane and so the lumbar spine is progressively extended as the direction of the force progressively inclines. Anatomical, physical dynamics tend to apply the force, as its direction progressively ascends, progressively higher along the lumbar spine, i.e., toward the L1 vertebra. This may be seen by recognising that the direction of the force is initially misaligned with the predominant line of the lumbar spine. In consequence, the force is applied more heavily toward the base of the lumbar spine, i.e., toward L5. As the direction of the force ascends, the direction lies progressively closer to the predominant line of the lumbar spine. With the force more aligned with the lumbar spine, the force is applied more evenly to each lumbar vertebra and hence more of the force reaches the upper lumbar vertebrae. This ascending change in vectors targets vertebral segments higher in the lumbar vertebral chain. The extending force will apply more force at the anterior border of the annulus and so may open disc spaces higher in the lumbar chain anteriorly.

FIG. 12 illustrates (the spine of a person in the prone position and) the situation where the direction of the force progressively descends while the magnitude of the force increases. This tends to decrease the lordotic curvature of the lumbar spine; thus the lumbar spine is progressively flexed as the direction of the force descends. Anatomical, physical dynamics (as the force becomes progressively more misaligned with the predominant line of the lumbar spine) tend to apply this changing force progressively lower along the lumbar spine, i.e., toward the L5 vertebra. The flexing force will apply more force at the posterior border of the annulus and so may open disc spaces lower in the lumbar chain posteriorly.

If the patient were lying in a supine position on table 10 and tethered to the tensionometer-head 36 of the table 10 with a pelvic harness 62 as shown in FIG. 3, applying a progressively greater, progressively more upwardly directed forces progressively flexes the lumbar spine. Anatomical, physical dynamics tend to apply this changing force progressively lower along the lumbar spine. On the other hand, with the patient tethered to the table in this manner, applying a progressively greater, progressively more downwardly directed force progressively extends the lumbar spine and anatomical, physical dynamics tend to apply this changing force progressively higher along the lumbar spine.

Figure 13:
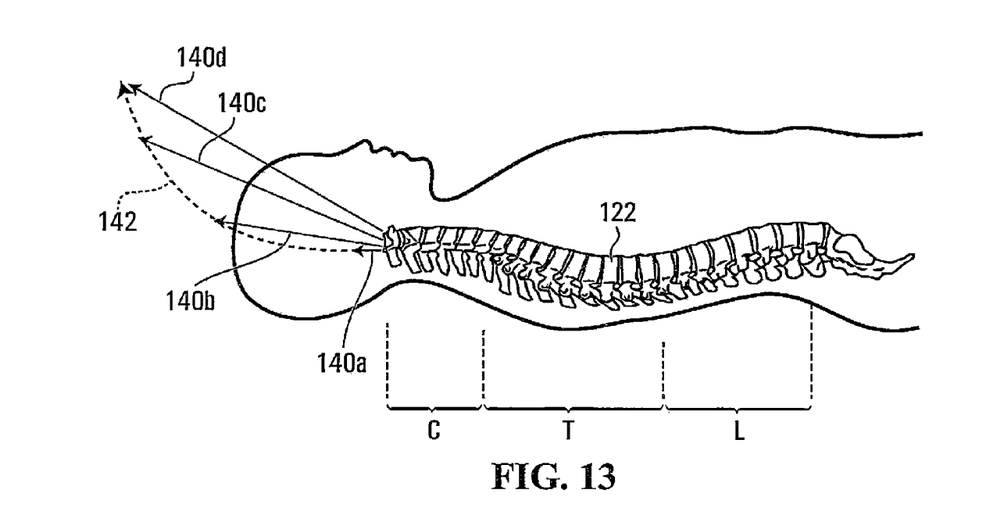

With a patient lying in a supine position on table 10 and tethered to the tensionometer-head 36 of the table 10 with a cervical-head harness 70 as shown in FIG. 4, FIG. 13 shows the ascending force vectors 140a, 140b, 140c, 140d progressively applied to the patient's spine during logarithmic tension increase where the tensionometer-head 36 follows an ascending arc 142. During cervical spine treatments, the use of a full ascending curve (arc) progressively flexes the cervical spine from C2-C3 to C7-T1 as the tension increases gradually.

Figure 14:
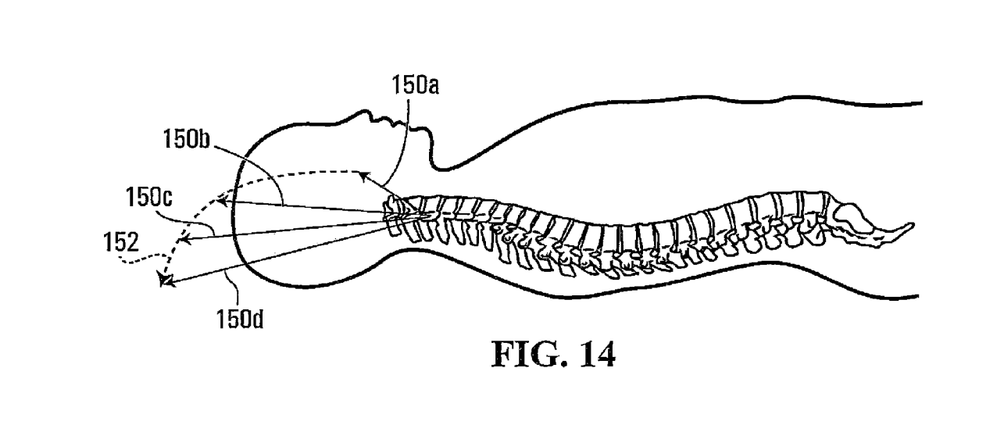

FIG. 14 shows the force vectors 150a, 150b, 150c, 150d progressively applied to the patient's spine during logarithmic tension increase where the tensionometer-head 36 follows a descending arc 152. These force vectors lie in the mid-sagittal plane of the patient and, with the table top horizontal, this mid-sagittal plane will be a vertical plane.

The progressively directionally ascending and strengthening force illustrated in FIG. 13 progressively pulls and rotates the cervical spine in flexion and so tends to decrease the lordotic curvature of the cervical spine C on an anterior/posterior plane. During application of this force, the thoracic spinal chain is essentially immobile due to the connections of the thoracic spine to the rib cage. Anatomical, physical dynamics tend to apply the force, as its direction progressively ascends (and the cervical vertebrae chain is progressively "straightened out"), progressively lower along the cervical spine, i.e., toward the C7 vertebra.

A downward dynamic curve as shown in FIG. 14 pulls and rotates the cervical spine and patient's head in extension. This will tend to increase the curvature of the cervical spine. Anatomical, physical dynamics tend to apply the force, as its direction progressively descends, progressively higher along the cervical spine.

The logarithmic distraction force decompresses the spinal column and hence is a decompression force. Because changing the direction of the force changes which vertebrae are most exposed to the force, judicious selection of the starting height and ending height of the tensionometer-head 36 (and therefore the final direction of the force) allows a decompressive force to be selectively focused on different vertebral segments of the cervical or lumbar spine. This is in contrast to known tables which linearly apply a distraction force to the spine; with these known tables, the distracting force will be applied more or less evenly along the vertebral chain. In another mode of operation, table 10 may apply a logarithmic or linearly increasing uni-directional force by selecting a fixed vertical height of adjustable support 30.

Figure 15:
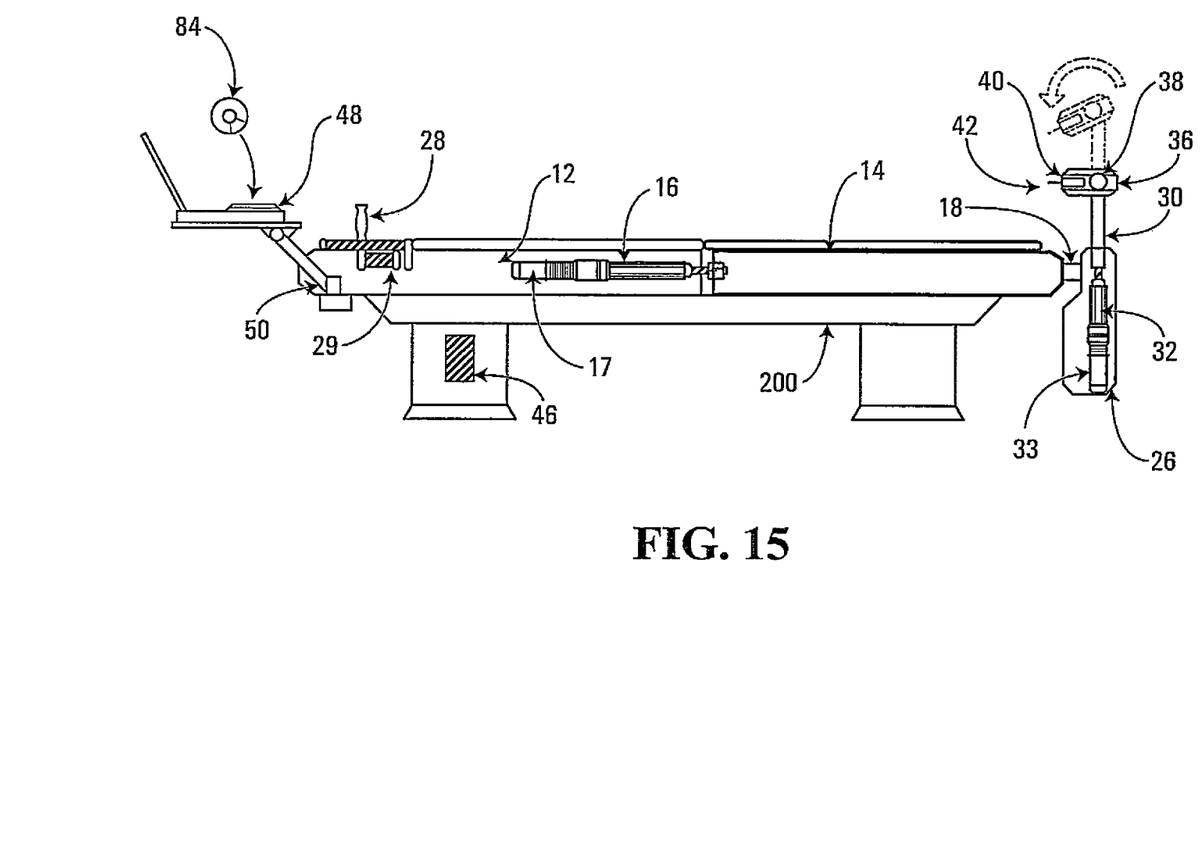
FIG. 15 is a schematic side view of a vertebral decompression table made in accordance with another embodiment of this invention.

A suitable function for time versus tension for the logarithmic decompression phase is described in U.S. Pat. No. 6,039,737 issued Mar. 21, 2000, the contents of which are incorporated herein by reference. The same function may be used for the logarithmic tension retraction phase [0039] Turning to FIG. 15, where like parts have been given like reference numerals, vertebral decompression table 200 differs from the table 10 of FIG. 1 in that linear actuator 22 and its arm 18 are omitted and the base 26 of vertically adjustable support 30 is joined directly to the moveable table section 14. With this arrangement, linear actuator 16 is used to separate the table halves to establish and maintain a pre-tension and as well, linear actuator 16, along with linear actuator 32, operate, under control of controller 46, to produce the logarithmic directionally changing forces hereinbefore described.

Figure 16:
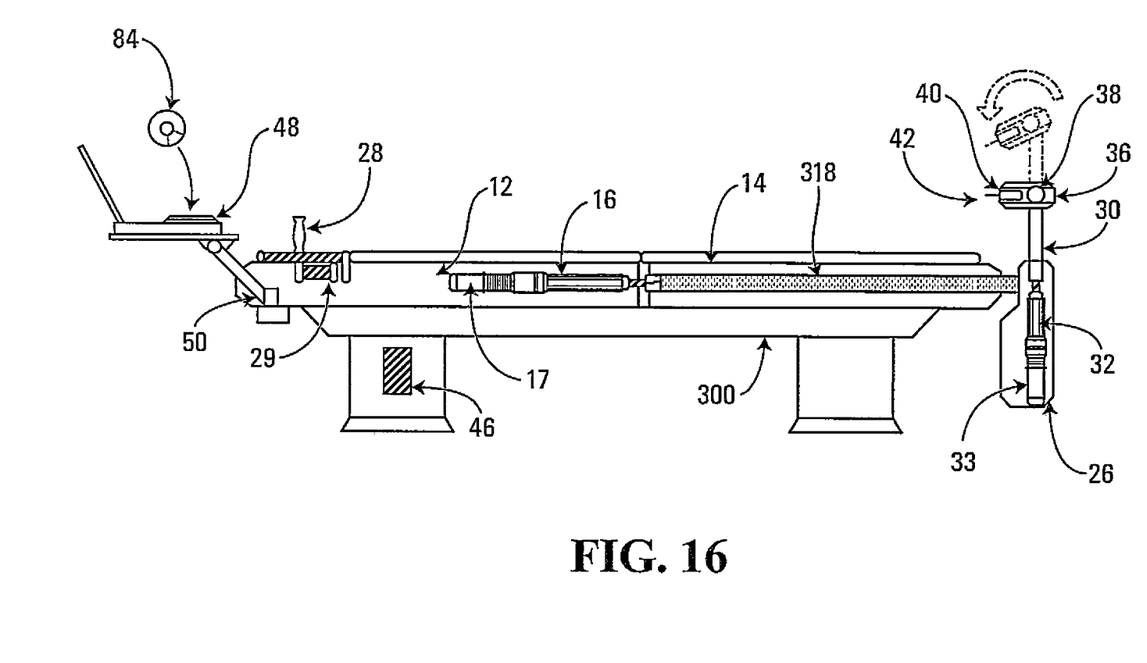
FIG. 16 is a schematic side view of a vertebral decompression table made in accordance with a further embodiment of this invention.

Turning to FIG. 16, where like parts have been given like reference numerals, a vertebral decompression table 300 differs from the table 10 of FIG. 1 in two respects: firstly, linear actuator 22 and its arm 18 are omitted and, secondly, linear actuator 16 is provisioned with a reciprocating arm 318 which extends through the moveable table section 14 to join to the base 26 of vertically adjustable support 30. With this arrangement, the controller 46 controls the linear actuator 16 to apply a pre-tension and then controls both linear actuator 16 and 32 to apply the aforedescribed logarithmic directionally changing forces. In doing so, moveable table section 14 may passively slide with the patient. With this embodiment, it would be possible to provide a table which has no moveable section, but this would have the drawback that the table would then frictionally engage the patient and distort the applied forces.

While the table has been described with linear actuators as drives, obviously any other controllable drive may be substituted as, for example, hydraulic cylinders and/or belt drives and/or pulleys.

While the retraction phase has been described as a logarithmic phase, alternatively, tension could be released linearly rather than logarithmically.

Other modifications will be apparent to those skilled in the art and, therefore, the invention is defined in the claims.

What is claimed is:

1. A method of applying tension to a spinal column of a patient, comprising:
pulling a tether attached to said patient with a harness to apply a progressively increasing vertebral decompression force at a progressively changing angle with respect to a predominant line of said spinal column, said force lying in a sagittal plane of said patient, and said force increasing at a logarithmic rate.

2. The method of claim 1 wherein said sagittal plane is a vertical plane and said progressively changing angle is a progressively increasing angle.

3. The method of claim 1 wherein said sagittal plane is a vertical plane and said progressively changing angle is a progressively decreasing angle.

4. The method of claim 1 wherein said progressively changing angle is a first angle and is one of a progressively increasing angle and a progressively decreasing angle and further comprising:
   after reaching a maximum force, progressively decreasing said decompression force at a progressively changing second angle, said second angle being another of a progressively-increasing angle and a progressively decreasing angle.

5. The method of claim 4 further comprising:
   applying a decompressing pre-tension prior to said applying said logarithmically increasing decompression force.

6. The method of claim 5 wherein said progressively decreasing said decompression force decreases said decompression force to said pre-tension.

7. The method of claim 4 wherein said progressively decreasing said decompression force comprises decreasing said decompression force logarithmically.

8. The method of claim 1 wherein said logarithmically increasing decompression force is applied through a harness.

9. The method of claim 8 wherein said harness is a cervical-head harness comprising a cervical support collar having a first pair of attachment points extending on either side of a patient's head below said patient's mandible and between said patient's chin and ear and a second pair of attachment points lying on either side of said patient's head proximate a back of said patient's head and straps attaching to each attachment point.

10. The method of claim 9 wherein said straps are adjustable and further comprising adjusting said straps to selectively control application of forces through said cervical-head harness.

11. The method of claim 8 wherein said harness is a pelvic harness.

12. The method of claim 6 further comprising, after said decreasing said decompression force to said pre-tension, repeating said applying said logarithmically increasing decompression force and, after reaching a maximum force, said progressively decreasing said decompression force to said pre-tension.

13. The method of claim 1 further comprising measuring tension applied to said spinal column.

14. The method of claim 13 wherein said increasing vertebral decompression force is applied by drives and further comprising outputting a measurement of said tension to a microprocessor controlling said drives.

15. A method of applying tension to the spinal column of a patient, comprising:
   pulling a tether attached to said patient with a harness to apply a progressively increasing vertebral decompression force and simultaneously progressively changing an angle of the applied force with respect to a predominant line of said spinal column so that the applied force increases at a logarithmic rate.

16. The method of claim 15 wherein said force is applied in a saggital plane of said patient and the angle of force applied in said saggital plane is progressively changed from a smaller angle to a larger angle.

17. The method of claim 15 wherein said force is applied in a saggital plane of said patient and the angle of force applied in said saggital plane is progressively changed from a larger angle to a smaller angle.

* * * * *